(12) United States Patent
Lee et al.

(10) Patent No.: US 9,011,921 B2
(45) Date of Patent: Apr. 21, 2015

(54) SUSTAINED-RELEASE POLYMERIC MICROPARTICLES CONTAINING POORLY WATER-SOLUBLE DRUG AND METHOD FOR PREPARING THE SAME

(75) Inventors: Sa Won Lee, Daejeon (KR); Do Hoon Kim, Seoul (KR); Bong Oh Kim, Daejeon (KR); Min Hyo Seo, Daejeon (KR)

(73) Assignee: Samyang Biopharmaceuticals Corporation, Seoul (KR)

( * ) Notice: Subject to any disclaimer, the term of this patent is extended or adjusted under 35 U.S.C. 154(b) by 0 days.

(21) Appl. No.: 13/995,727

(22) PCT Filed: Dec. 23, 2011

(86) PCT No.: PCT/KR2011/010030
§ 371 (c)(1),
(2), (4) Date: Jun. 26, 2013

(87) PCT Pub. No.: WO2012/087062
PCT Pub. Date: Jun. 28, 2012

(65) Prior Publication Data
US 2013/0273167 A1  Oct. 17, 2013

(30) Foreign Application Priority Data

Dec. 24, 2010 (KR) ........................ 10-2010-0134633

(51) Int. Cl.
*A61K 9/50* (2006.01)
*A61K 47/34* (2006.01)
(Continued)

(52) U.S. Cl.
CPC ............... *A61K 47/34* (2013.01); *A01N 25/28* (2013.01); *A61K 9/1694* (2013.01);
(Continued)

(58) Field of Classification Search
CPC .... A01N 25/28; A61K 9/1647; A61K 9/1694
See application file for complete search history.

(56) References Cited

U.S. PATENT DOCUMENTS 6,630,156 B1    10/2003  Seo et al.
2004/0247561 A1*  12/2004  Seo et al. ................... 424/78.27
(Continued)

FOREIGN PATENT DOCUMENTS

JP          9-221420 A    8/1997
JP           10-7583 A    1/1998
(Continued)

OTHER PUBLICATIONS

Eerdekens, M. et al, "Pharmacokinetics and tolerability of long-acting risperidone in schizophrenia," Schizophrenia Research, 2004, vol. 70, pp. 91-100.
(Continued)

*Primary Examiner* — Carlos Azpuru
(74) *Attorney, Agent, or Firm* — Birch, Stewart, Kolasch & Birch, LLP

(57) ABSTRACT

A sustained-release microparticle containing a poorly water-soluble drug is disclosed. The sustained-release microparticle containing a poorly water-soluble drug has a multivalent metal ion salt of polylactic acid having at least one terminal carboxyl group or a derivative thereof. The poorly water-soluble drug is entrapped in the multivalent metal ion salt of polylactic acid or a derivative thereof The polylactic acid has at least one terminal carboxyl group or a derivative thereof has an average molecular weight number from 500 to 5,000 daltons. A method for preparing a sustained-release polymeric microparticles containing a poorly water-soluble drug is provided.

17 Claims, 2 Drawing Sheets

(51) Int. Cl.
  *A01N 25/28* (2006.01)
  *A61K 9/16* (2006.01)
  *A61K 31/175* (2006.01)
  *A61K 31/27* (2006.01)
  *A61K 31/436* (2006.01)
  *A61K 31/485* (2006.01)
  *A61K 31/519* (2006.01)
  *A61K 31/565* (2006.01)
  *A61K 31/57* (2006.01)
  *A61K 31/554* (2006.01)

(52) U.S. Cl.
  CPC ............ *A61K 9/1635* (2013.01); *A61K 9/1647* (2013.01); *A61K 31/175* (2013.01); *A61K 31/27* (2013.01); *A61K 31/436* (2013.01); *A61K 31/485* (2013.01); *A61K 31/519* (2013.01); *A61K 31/565* (2013.01); *A61K 31/57* (2013.01); *A61K 31/554* (2013.01)

(56) References Cited

U.S. PATENT DOCUMENTS

2004/0253195 A1* 12/2004 Seo et al. ................... 424/70.11
2005/0226932 A1    10/2005 Yoon et al.
2013/0274188 A1* 10/2013 Yi et al. ........................ 514/7.7

FOREIGN PATENT DOCUMENTS

| | | |
|---|---|---|
| JP | 11-322631 A | 11/1999 |
| JP | 2003-171264 A | 6/2003 |
| JP | 2003-212758 A | 7/2003 |
| JP | 2005-505674 A | 2/2005 |
| JP | 2006-28031 A | 2/2006 |
| WO | WO 03/033592 A1 | 4/2003 |
| WO | WO 2005/081825 A2 | 9/2005 |
| WO | WO 2005/107813 A1 | 11/2005 |
| WO | WO 2010/074380 A1 | 7/2010 |

OTHER PUBLICATIONS

Keith, S. et al, "Advances in psychotropic formulations," Progress in Neuro-Psychopharmacology & Biological Psychiatry, 2006, vol. 30, pp. 996-1008.

International Search Report, mailed Jun. 21, 2012, issued in PCT/KR2011/010030.

European Search Report dated Oct. 22, 2014 for EP Application No. 11850838.1.

* cited by examiner

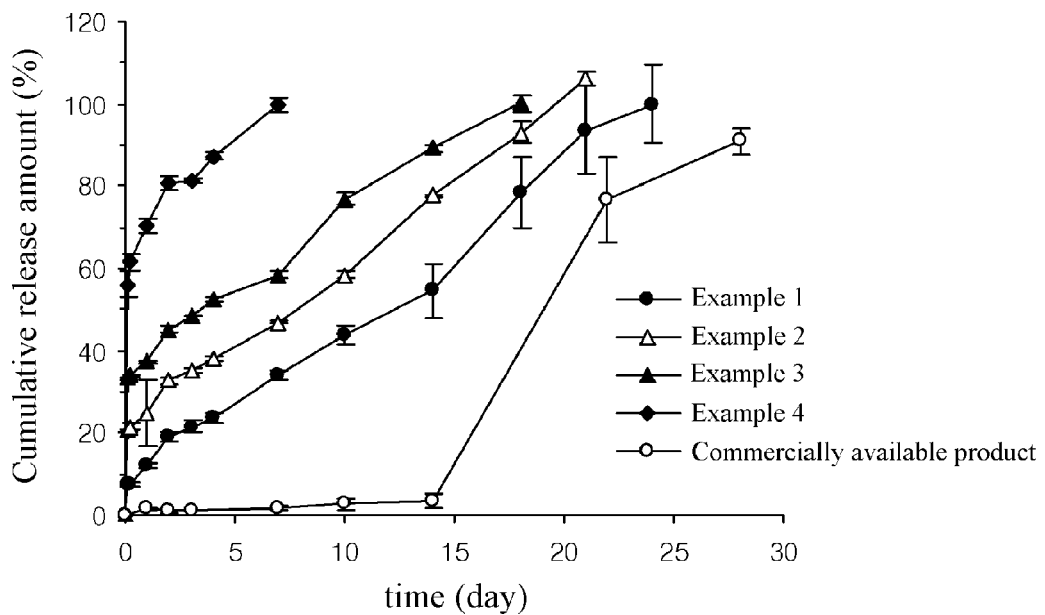
Fig. 4
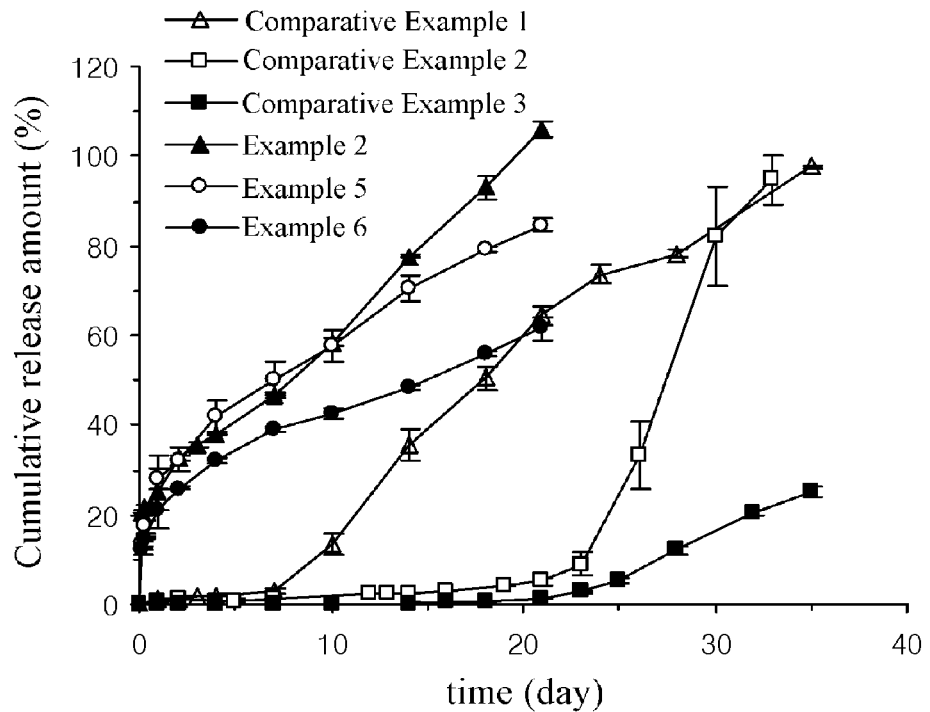
Fig. 5]

SUSTAINED-RELEASE POLYMERIC MICROPARTICLES CONTAINING POORLY WATER-SOLUBLE DRUG AND METHOD FOR PREPARING THE SAME

TECHNICAL FIELD

The present invention relates to sustained-release polymeric microparticles containing a poorly water-soluble drug and a method for preparing the same. More specifically, the present invention relates to polymeric microparticles which comprise a multivalent metal cation salt of polylactic acid having at least one terminal carboxyl group or a derivative thereof wherein the poorly water-soluble drug is entrapped in the multivalent metal cation salt of polylactic acid or a derivative thereof, by which the constant release rate and effective in-blood concentration of drug can be maintained continuously without initial burst or delayed release of drug. Accordingly, the microparticles of the present invention and the method for preparing the same can be effectively used for long-term sustained-release formulations of poorly water-soluble drugs.

BACKGROUND ART

In case of drugs for treating chronic diseases, in order to reduce dose frequency they are prepared as sustained-release formulations, by which a therapeutically effective drug concentration can be maintained for a long period of time even by single administration only, and compliance of patients to drug therapy can be improved. Among such sustained-release formulations, polymeric microspheres have received considerable attention from many pharmaceutical companies. Examples of currently commercially available polymeric microsphere products include Risperdal Consta which is a two-week release formulation of Risperidone for treating schizophrenia, and Vivitrol which is a four-week release formulation of naltrexone for drug addiction. These formulations are typical poly(lactide-co-glycolide) (PLGA) microsphere formulations. However, they do not well release the drug at an initial stage after drug administration and the release is delayed by one to four weeks. Thus, they have to be administered inconveniently along with an oral formulation in order to obtain rapid efficacy at the initial stage.

Examples of biodegradable polymers used for preparation of microspheres include polylactide, polyglycolide, poly(lactide-co-glycolide) (PLGA) and the like. These biodegradable polymers commonly have a molecular weight of 100,000 to 200,000 daltons. The polymers have at least one terminal carboxyl acid and are thus acidic in an aqueous solution, and release organic acid such as lactic acid or glycolic acid when hydrolyzed and thus cause the neighboring environment to become acidic. For this reason, these polymers are disadvantageously unsuitable for use in drugs which are unstable to acids. In addition, since the molecular weight is considerably large, it is not easy to synthesize them as standardized polymers with uniform physical and chemical properties. For this reason, when the used batch of synthesized polymer is changed, drug release pattern from the microsphere prepared therefrom are also changed, and thus it is not easy to maintain the drug release patterns constantly. Furthermore, in order to synthesize biodegradable polymers with high molecular weight, it is necessary to use ring-opening polymerization utilizing cyclic dimers such as lactide or glycolide, the method of which requires that the synthesis be conducted in an anhydrous state. Thus, a mass-production by this method is relatively difficult. In addition, when hydrophobic drugs are applied, the polymer of microspheres starts to degrade after a predetermined time and so it is disadvantageous in that the drug efficacy is not exhibited immediately after the administration. For example, Risperdal Consta starts to release the drug about two weeks after the administration and thus it is sometimes needed to administer an oral drug for that period (M. Eerdekens et al./Schizophrenia Research 70 (2004) 91-100; S. Keith/Progress in Neuro-Psychopharmacology & Biological Psychiatry 30 (2006) 996-1008).

Accordingly, although hydrophobic drugs are applied, there is a need for development of sustained-release microparticle having a release profile in which the initial release is smoothly performed after drug administration and a level of drug in blood can be effectively maintained for a long period of time.

DISCLOSURE OF INVENTION

Technical Problem

As a result of intensive research to develop techniques to effectively control the release rate of drugs from microparticles, the inventors of the present invention discovered that the release rate and amount of drugs can be readily controlled by substituting monovalent metal ions in monovalent metal salts of biodegradable polymers having a molecular weight of 5,000 daltons or less, which can be easily standardized and produced in a large scale, with multivalent metal ions, and adjusting the molecular weight of the polymers and a ratio between the drug and the polymer, and have completed the present invention.

Therefore, it is an object of the present invention to provide sustained-release polymeric microparticles containing a poorly water-soluble drug, using a biodegradable polymer having a molecular weight of 500 to 5,000 daltons which can be easily standardized and produced in a large scale, by which excessively delayed release of drug can be prevented and a concentration of drug in blood can be increased within a short time to an effective level, and the release profile maintaining the effective drug concentration in blood for a long period of time can be obtained; and a method for preparing the same.

Solution to Problem

In accordance with one aspect of the present invention, provided is a sustained-release microparticle containing a poorly water-soluble drug, comprising the poorly water-soluble drug and a multivalent metal ion salt of polylactic acid having at least one terminal carboxyl group or a derivative thereof, wherein the poorly water-soluble drug is entrapped in the multivalent metal ion salt of polylactic acid or a derivative thereof.

In accordance with another aspect of the present invention, provided is a method for preparing a sustained-release microparticle containing a poorly water-soluble drug, comprising: i) preparing a polymer-drug solution containing a monovalent metal salt of polylactic acid having at least one terminal carboxyl group or a derivative thereof and the poorly water-soluble drug in an organic solvent; and ii) dispersing the polymer-drug solution in an aqueous solution containing a multivalent metal ion and optionally a surfactant to form a microparticle.

Advantageous Effects of Invention

The present invention provides microparticles which easily control drug release, maintain effective drug concentration in blood for a long period of time and are thus suitable for use in sustained-release formulations of drugs requiring frequently repeated administration.

BRIEF DESCRIPTION OF DRAWINGS

FIG. 4 is a graph showing the change of the release amount of drug according to the change in ratio of drug to polymer in Test Example 3 (release test).

FIG. 5 is a graph showing the change of the release amount of drug according to the change in molecular weight of polymer while constantly maintaining the ratio of drug to polymer in Test Example 3 (release test).

MODE FOR THE INVENTION

Figure 1:
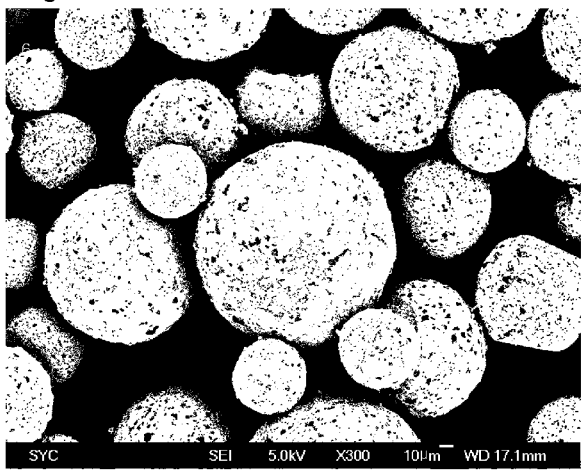
FIG. 1 is a scanning electronic microscope (SEM) image showing microparticles prepared in Example 2 of the present invention.

Hereinafter, the present invention will be described in detail.

In the present invention, specific examples of the polylactic acid having at least one terminal carboxyl group or a derivative thereof include one or more selected from the group consisting of polylactic acid, polylactide, polyglycolide, polymandelic acid, polycaprolactone, polyanhydride and copolymers thereof.

The remaining terminal group(s) other than the terminal carboxyl group(s) of the polylactic acid or a derivative thereof is one or more terminal groups selected from the group consisting of hydroxy, acetoxy, benzoyloxy, decanoyloxy, palmitoyloxy, methyl and ethyl.

The number average molecular weight of the polylactic acid or a derivative thereof used for the microparticles according to the present invention can be adjusted by controlling reaction temperature, time, etc. during the preparation process, and is preferably 500 to 5,000 daltons, and more preferably 2,000 to 5,000 daltons. When the molecular weight is lower than 500 daltons, it may be difficult to expect the sustained drug release. When the molecular weight is higher than 5,000 daltons, it may not be easy to synthesize the polymer as standardized polymer having uniform physical and chemical properties. Furthermore, in case of the high molecular weight polymer, the synthesis should be performed under anhydrous conditions and mass-production may be thus difficult. However, the biodegradable polymer having the above molecular weight range can be prepared by synthesizing organic acid monomers such as lactic acid or glycolic acid by co-condensation polymerization, and in this case it is not necessary to maintain anhydrous conditions, and mass-production is thus relatively easy.

In the present invention, the polylactic acid having at least one terminal carboxyl group or a derivative thereof is preferably one or more selected from the group consisting of Formulae 1 to 6 below:

$$RO-CHZ-[A]_n-[B]_m-COOM \qquad \text{[Formula 1]}$$

wherein A is —COO—CHZ—; B is —COO—CHY—, —COO—CH$_2$CH$_2$CH$_2$CH$_2$CH$_2$— or —COO—CH$_2$CH$_2$OCH$_2$—; R is hydrogen atom, or acetyl group, benzoyl group, decanoyl group, palmitoyl group, methyl group, or ethyl group; each of Z and Y independently is hydrogen atom, methyl group or phenyl group; M is independently H, Na, K, or Li; n is an integer of 1 to 30; and m is an integer of 0 to 20;

$$RO-CHZ-[COO-CHX]_p-[COO-CHY']_q-COO-CHZ-COOM \qquad \text{[Formula 2]}$$

wherein X is methyl group; Y' is hydrogen atom or phenyl group; p is an integer of 0 to 25 and q is an integer of 0 to 25 provided that p+q is an integer of 5 to 25; R is hydrogen atom, acetyl group, benzoyl group, decanoyl group, palmitoyl group, methyl group or ethyl group; Z is hydrogen atom, methyl group or phenyl group; and M is independently H, Na, K, or Li;

$$RO\text{-}PAD\text{-}COO\text{-}W\text{-}M' \qquad \text{[Formula 3]}$$

wherein W-M' is

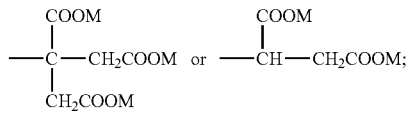

PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one; R is hydrogen atom, acetyl group, benzoyl group, decanoyl group, palmitoyl group, methyl group or ethyl group; and M is independently H, Na, K, or Li;

$$S\text{—O-PAD-COO-Q} \qquad \text{[Formula 4]}$$

wherein S is

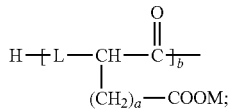

L is —NR$_1$— or -O- in which R$_1$ is hydrogen atom or C$_{1-10}$ alkyl; Q is CH$_3$, CH$_2$CH$_3$, CH$_2$CH$_2$CH$_3$, CH$_2$CH$_2$CH$_2$CH$_3$, or CH$_2$C$_6$H$_5$; a is an integer of 0 to 4; b is an integer of 1 to 10; M is H, Na, K, or Li; PAD is one or more selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one;

[Formula 5]

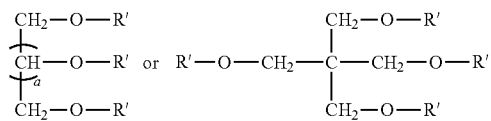

wherein R' is —PAD-O—C(O)—CH$_2$CH$_2$—C(O)—OM, in which PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one, and M is H, Na, K, or Li; and a is an integer of 1 to 4, for example, 3-arm PLA-COONa provided a=1,4-arm PLA-COONa provided a=2,5-arm PLA-COONa provided a=3, and 6-arm PLA-COONa provided a=4;

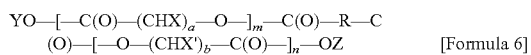  [Formula 6]

wherein each of X and X' is independently hydrogen, alkyl (for example, alkyl having 1 to 10 carbon atoms such as methyl) or aryl (for example, aryl having 6 to 20 carbon atoms such as phenyl); each of Y and Z is independently H, Na, K, or Li; each of m and n is independently an integer of 0 to 95, provided that 5<m+n≤100; each of a and b is independently an integer of 1 to 6; R is substituted or unsubstituted —(CH$_2$)$_k$— in which k is an integer of 0 to 10, divalent alkenyl having 2 to 10 carbon atoms, divalent aryl having 6 to 20 carbon atoms, or a combination thereof.

In one embodiment of the present invention, the multivalent metal ion salt of polylactic acid or a derivative thereof is a multivalent metal salt of water-insoluble polylactic acid or a derivative thereof formed by ionically bonding the terminal carboxyl group of the polylactic acid or a derivative thereof to a divalent or trivalent metal ion.

The divalent or trivalent metal ion is preferably one or more selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$ and $Al^{3+}$. The divalent or trivalent metal ion may be provided as a form of sulfate salt, hydrochloride salt, carbonate salt, phosphate salt or hydroxide, preferably, as a form of $CaCl_2$, $MgCl_2$, $ZnCl_2$, $AlCl_3$, $FeCl_3$, $CaCO_3$, $MgCO_3$, $Ca_3(PO_4)_2$, $Mg_3(PO_4)_2$, $AlPO_4$, $MgSO_4$, $Ca(OH)_2$, $Mg(OH)_2$, $Al(OH)_3$, or $Zn(OH)_2$.

In the microparticle of the present invention, the multivalent metal ion salt of polylactic acid or a derivative thereof may be contained in an amount of 50 to 99% by weight with respect to the total weight of the microparticle. When the content of the polymer is less than 50% by weight, the sustained release effects may not be obtained, and when the content is greater than 99% by weight, it may disadvantageously exceed a dose that can be administered once by a common method.

In the present invention, the poorly water-soluble drug means a hydrophobic drug having a water solubility (25° C.) of 100 mg/mL or less. Specific examples thereof include olanzapine, risperidone, ziprasidone, rivastigmine, naloxone, naltrexone, sirolimus, tacrolimus, carmustine, progesterone, estrogen, estradiol, levonorgestrel, norethisteron and the like. In a preferred embodiment of the present invention, risperidone is used. The content of the poorly water-soluble drug in the microparticle of the present invention may be 1 to 50% by weight of the total weight of the microparticle, but is not particularly limited thereto. When the content is less than 1% by weight, the intended pharmaceutical effects may not be obtained, and when the content is greater than 50% by weight, a problem of initial burst of drug may occur.

The microparticle of the present invention may have a particle diameter of, for example, 1 to 400 µm, specifically 5 to 250 µm, and more specifically 50 to 150 µm. It has an amorphous or spherical shape in which a poorly water-soluble drug is entrapped in the inner core of microparticle comprising the multivalent metal ion salt of polylactic acid or a derivative thereof.

As used herein, the terms "sustained-release," "sustained-release delivery" and "sustained-release drug delivery" mean that the effective concentration of a drug in blood is maintained for a long period of time, for example, 72 hours or longer, by single administration. The administration route may be subcutaneous, intramuscular or intravenous injection. Inconvenience caused by frequent administration can be solved by sustained-release delivery.

In addition to the ingredients explained above, the microparticle of the present invention may further contain one or more pharmaceutical additives such as a preservative, a stabilizing agent, a hydrating agent or a salt and/or a buffer for controlling osmotic pressure, or other therapeutically effective substances. The microparticle of the present invention may be dispersed, delivered or applied to the target site of the subject through a delivery route such as injection and/or subcutaneous, intramuscular, intraabdominal or dermal implant, and intramucosal administration. For example, the microparticle of the present invention may be administered in the form of a homogeneous suspension in a dispersion media such as an injection solution. Examples of the dispersion media include distilled water for injection, 5% glucose, physiological saline, mineral oils, and mono-, di- and tri-glycerides and the like.

In another aspect of the present invention, provided is a method for preparing a sustained-release microparticle containing a poorly water-soluble drug, comprising: i) preparing a polymer-drug solution containing a monovalent metal salt of polylactic acid having at least one terminal carboxyl group or a derivative thereof and the poorly water-soluble drug in an organic solvent; and ii) dispersing the polymer-drug solution in an aqueous solution containing a multivalent metal ion and optionally a surfactant to form a microparticle.

The preparation method of microparticle according to the present invention is characterized in that the addition of the monovalent metal salt of polylactic acid or a derivative thereof to an aqueous solution of the multivalent metal ion converts the monovalent metal salt of polylactic acid or a derivative thereof into a multivalent metal salt of water-insoluble polylactic acid or a derivative thereof, which is then precipitated and forms the microparticles.

The method for preparing microparticle of the present invention will be described in detail step by step.

First Step: Preparation of Polymer-Drug Solution

The preparation of a polymer-drug solution containing a monovalent metal salt of polylactic acid or a derivative thereof and a poorly water-soluble drug in an organic solvent may be carried out in any one of the following three manners.

i-1) Dissolving a monovalent metal salt of polylactic acid or a derivative thereof in an organic solvent to prepare a biodegradable polymer solution and adding a poorly water-soluble drug to the biodegradable polymer solution to prepare a solution containing the polymer and drug i-2) Dissolving a poorly water-soluble drug in an organic solvent to prepare a drug solution and adding a monovalant metal salt of polylactic acid or a derivative thereof to the drug solution to prepare a solution containing the polymer and drug i-3) Dissolving a monovalant metal salt of polylactic acid or a derivative thereof and a poorly water-soluble drug in an organic solvent together to prepare a solution containing the polymer and drug That is, the preparation of the sustained-release composition of the present invention may be carried out by using polylactic acid having terminal carboxylic acid group or a derivative thereof as a starting material (i-1), or starting with polylactic acid having at least one terminal carboxylic acid group or a derivative thereof and neutralizing it with an alkali metal salt to convert it into a monovalent metal salt of polylactic acid or a derivative thereof, and then using the monovalant metal salt (i-2 and i-3). The alkali metal salt may be provided from sodium carbonate, sodium hydrogen carbonate, potassium hydrogen carbonate, potassium carbonate or the like.

The monovalant metal salt of polylactic acid or a derivative thereof can be obtained by neutralizing the corresponding polylactic acid having at least one terminal carboxylic acid group or a derivative thereof, such as compounds of Formula 1 to 6 wherein M is H, with a salt of alkali metal such as sodium, potassium or lithium where the salt of alkali metal may be provided from sodium carbonate, sodium hydrogen carbonate, potassium hydrogen carbonate, potassium carbonate or the like. Accordingly, the monovalant metal salt of polylactic acid or a derivative thereof used for the preparation method of microparticle according to the present invention may be any one of the compounds of Formulae 1 to 6 wherein M is Na, K, or Li.

Examples of the poorly water-soluble drug that can be used in the preparation method of microparticle according to the present invention may be those explained above. In one embodiment of the preparation method of microparticle of the present invention, the poorly water-soluble drug is used in an amount of 0.01 to 0.5 parts by weight, with respect to one part by weight of the monovalant metal salt of polylactic acid or a derivative thereof.

Examples of the organic solvent that can be used in the preparation method of microparticles according to the present invention include dichloromethane, hexafluoroisopropanol, ethyl acetate, ethanol, methanol, dimethylformamide, acetone, acetonitrile, tetrahydrofuran, acetic acid, dimethyl sulfoxide, chloroform, methyl dichloroacetate, methyl chloroacetate, ethyl chloroacetate, ethyl dichloroacetate, methyl fluoroacetate, methyl difluoroacetate, ethyl fluoroacetate, ethyl difluoroacetate, ethyl acetate, methyl acetate, methyl formate, ethyl formate, isopropyl formate, propyl formate and mixtures thereof. The organic solvent can be suitably selected in consideration of the biodegradable polymer, drug solubility, biocompatibility and the like. Specifically, dichloromethane, acetone and a mixture thereof, which have a low boiling point and thus can be easily removed, may be used. The organic solvent may be used in an amount of 0.5 to 100 parts by weight with respect to one part by weight of the monovalent metal salt of polylactic acid or a derivative thereof.

Second Step: Formation of Microparticles

The polymer-drug solution prepared in the first step is dispersed in an aqueous solution containing multivalent metal cations to form microparticles.

In this step, when the polymer-drug organic solution is dispersed in the aqueous solution of multivalent metal ions, the monovalent metal ions in the monovalent metal salt of polylactic acid or a derivative thereof are substituted with divalent or trivalent metal ions to form a water-insoluble multivalent metal salt of polylactic acid or a derivative thereof, and such formed water-insoluble salt of polymer is precipitated and the microparticles entrapping a hydrophobic drug therein are thus obtained.

Examples of the multivalent metal cation that can be used in the preparation method of microparticles according to the present invention may be those explained above. When a bi- or trivalent metal ion is used, the use amount of multivalent metal cation is 0.5 to 5 equivalents, preferably 1 to 2 equivalents with respect to the carboxyl terminal group of the polylactic acid or a derivative thereof, to allow all of the carboxyl terminal groups of polylactic acid or a derivative thereof to be substituted with the bi- or trivalent metal ions.

The aqueous solution of the multivalent metal cation may optionally contain a surfactant to increase the microparticle formation yield and obtain uniform microparticles. Any surfactant conventionally used in the art may be used without particular limitation. Specifically, polymeric surfactants such as poloxamers, polyvinyl alcohol, polyoxyethylene sorbitan fatty acid esters, natural polymers such as gelatin, and alkali salts of higher fatty acid may be used. Such a surfactant may be used, for example, in an amount of 0.001 to 0.1 parts by weight with respect to one part by weight of water in the aqueous solution.

The method for preparing a sustained-release microparticle containing poorly water-soluble drug according to the present invention may further comprise iii) obtaining the microparticle formed in step ii) and washing it with water.

Furthermore, the method for preparing a sustained-release microparticle containing poorly water-soluble drug according to the present invention may further comprise iv) freeze-drying the microparticle washed in step iii). During the freeze-drying, an additive for freeze-drying may be added. The examples of the additive for freeze-drying include sugars, sugar alcohols or mixtures thereof. The sugar may be one or more selected from the group consisting of lactose, maltose, sucrose and trehalose, and the sugar alcohol may be one or more selected from the group consisting of mannitol, sorbitol, maltitol, xylitol and lactitol. In one embodiment of the present invention, the content of the additive for freeze-drying is 1 to 50% by weight, more preferably 1 to 30% by weight, based on the total dry weight of the freeze-dried composition.

Hereinafter, the present invention will be described in more detail with reference to the following Examples. However, the examples are provided to illustrate the present invention only and should not be construed as limiting the protection scope of the present invention.

EXAMPLES 1 to 6

Preparation of Drug-containing Microparticles

Polymeric microparticles of Examples 1 to 6 were prepared using polylactic acids having weight average molecular weights of 1,860, 3,400 or 4,220 daltons in accordance with the compositions set forth in the following Table 1. A blade of a homogenizer was placed at the point corresponding to ⅓ of the height from the bottom in a cylindrical reactor having a height of 150 mm and a diameter of 80 mm. 2 mL of dichloromethane was added to polylactic acid and risperidone in an organic phase vessel, followed by sealing the organic phase vessel and completely dissolving the ingredients. 500 mL of an aqueous solution of 1% (w/v) Poloxamer 188 containing calcium chloride was added to a reactor for preparing microparticles, and while stirring with 300 rpm rate the solution of risperidone and polymer in 2 mL of dichloromethane was slowly added thereto using a glass syringe to solidify microparticles. The solidified microparticles were screened by using a 38 to 200 μm sieving column and those having a particle size within this range were collected. The collected microparticles were washed with distilled water three times and freeze-dried for 24 hours to complete preparation. The microparticles were refrigerated prior to use. All of the above procedures were carried out by maintaining aseptic conditions at an aseptic worktable.

TABLE 1

| Examples | Risperidone mg | Risperidone % (w/w) | Sodium polylactate (mg) Molecular weight mg (Mn) | | Aqueous solution of Poloxamer 188 (mL)* | Calcium chloride (mg) | Dichloro-methane (mL) |
|---|---|---|---|---|---|---|---|
| Ex. 1 | 50  | 5  | 950 | 1,860 | 500 | 60 | 2 |
| Ex. 2 | 100 | 10 | 900 | 1,860 | 500 | 60 | 2 |
| Ex. 3 | 200 | 20 | 800 | 1,860 | 500 | 60 | 2 |
| Ex. 4 | 300 | 30 | 700 | 1,860 | 500 | 60 | 2 |
| Ex. 5 | 100 | 10 | 900 | 3,400 | 500 | 60 | 2 |
| Ex. 6 | 100 | 10 | 900 | 4,220 | 500 | 60 | 2 |

*0.1% (w/v)

COMPARATIVE EXAMPLES 1 to 3

Drug-containing PLGA Microspheres

Risperidone was dissolved in 3 mL of dichloromethane together with a polymer set forth in the following Table 2 to prepare a drug solution. Separately, a solution of 5% polyvinyl alcohol (PVA) was prepared by using a 0.02M carbonate buffer (0.02M $Na_2CO_3$+0.02M $NaHCO_3$). While stirring the 5% PVA solution at about 300 rpm, the drug solution was slowly injected into the PVA solution by using a glass syringe. After the incorporation of the drug solution was completed, the resulting solution was stirred at 300 rpm for one hour by using a stirrer to completely solidify microparticles. The solidified microparticles were screened by using a 38 to 200 μm sieving column and those having a particle size within this range were collected. The collected microparticles were washed with distilled water three times and freeze-dried for 24 hours to complete preparation. The microparticles were refrigerated prior to use. All of the above procedures were carried out by maintaining aseptic conditions at an aseptic worktable.

TABLE 2

| Comparative Examples | Risperidone mg | Risperidone wt % | PLGA (LA/GA = 75/25, 90K)$^a$ (mg) | PLGA (LA/GA = 75/25, 100K)$^a$ (mg) | PLGA (LA/GA = 75/25, 200K)$^a$ (mg) |
|---|---|---|---|---|---|
| Comp. Ex. 1 | 200 | 20 | 800 | — | — |
| Comp. Ex. 2 | 300 | 30 | — | 700 | — |
| Comp. Ex. 3 | 400 | 40 | — | — | 600 |

LA: lactic acid-derived unit
GA: glycolic acid-derived unit

TEST EXAMPLE 1

Evaluation of Shape and Surface State of Microparticles

Figure 2:
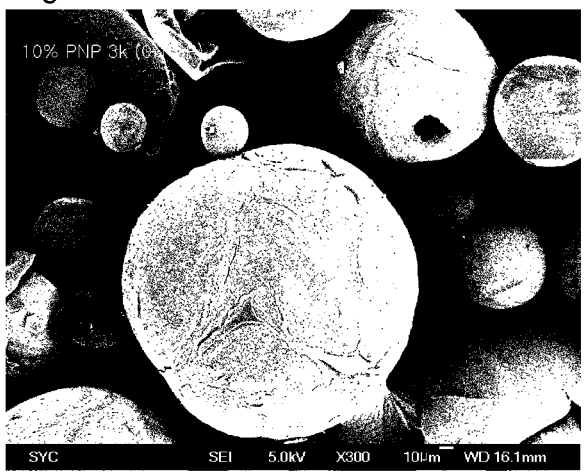
FIG. 2 is a scanning electronic microscope (SEM) image showing microparticles prepared in Example 5 of the present invention.
Figure 3:
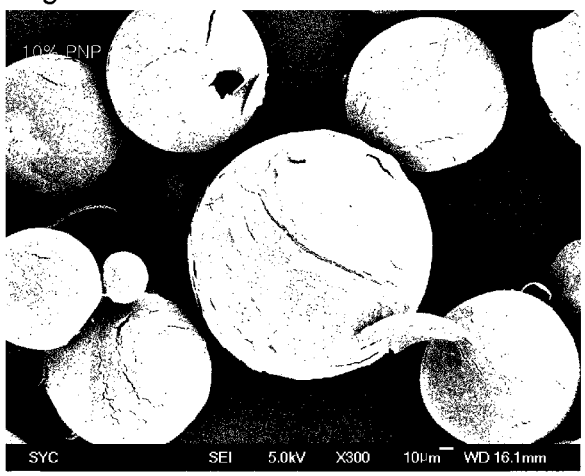
FIG. 3 is a scanning electronic microscope (SEM) image showing microparticles prepared in Example 6 of the present invention.

The microparticles prepared in Examples 2, 5 and 6 according to the present invention were imaged by using a scanning electron microscopy. The resulting images are shown in FIGS. 1 to 3, respectively. As can be seen from the images, all of the microparticles prepared in these Examples had a round shape and micropores on their surfaces. As the molecular weight increased, the size of micropore decreased and the surface became smoother.

TEST EXAMPLE 2

Content and Encapsulation Ratio of Drug

In order to measure the amount of risperidone encapsulated in microparticles, quantitative analysis was performed according to the following HPLC method. About 20 mg of microparticles prepared in Examples 1 to 6 and Comparative Examples 1 to 3 was added to a 20 mL flask, and acetonitrile was added thereto for complete dissolution with the total volume of 20 mL. The resulting solution was diluted 10 times with a mobile phase solution and filtered through 0.45 μm membrane filter paper, and 50 μL of the filtered solution was injected into HPLC.

HPLC Conditions
Column: Phenomenex Gemini-NX 5 u C18 110 Å (150× 4.6 mm)
Mobile phase: acetic acid buffer/methanol=600/400 (v/v)
Flow rate: 1 mL/min
Detector: UV 280 nm
Acetic acid buffer: solution of 6 g of ammonium acetate and 60 mL of acetic acid in 1.2 L of distilled water for injection In order to calculate the amount of the drug contained in the microparticles, the content of the drug in the microparticles and encapsulation ratio thereof were calculated in accordance with the following Equations 1 and 2. The results are shown in Table 3 below.

Content of drug (%)=amount of drug in microparticles/amount of microparticles×100   [Equation 1]

Encapsulation ratio of drug (%)=amount of actually encapsulated drug/amount of theoretically encapsulated drug×100   [Equation 2]

TABLE 3

| Examples | Drug loading % | Content (%) | Encapsulation ratio (%) |
|---|---|---|---|
| Ex. 1 | 5  | 4.55  | 91.00 |
| Ex. 2 | 10 | 8.20  | 82.00 |
| Ex. 3 | 20 | 16.13 | 80.65 |
| Ex. 4 | 30 | 22.86 | 76.20 |
| Ex. 5 | 10 | 9.47  | 94.70 |
| Ex. 6 | 10 | 9.66  | 96.60 |
| Comp. Ex. 1 | 20 | 17.73 | 88.65 |
| Comp. Ex. 2 | 30 | 25.97 | 86.57 |
| Comp. Ex. 3 | 40 | 32.90 | 82.25 |

TEST EXAMPLE 3

Release Test

The microparticles prepared in Examples 1 to 6 and Comparative Examples 1 to 3, and a commercially available product, Risperdal Consta, were subjected to in vitro drug release test. Specifically, to a test tube containing 500 mL of a pH 7.4 phosphate buffer solution, microparticles were added in an amount corresponding to 20 mg of the drug, and the tube was capped and the drug was allowed to be released continuously for 30 days or longer in a thermostatic chamber at 37° C. with a rotation speed of 60 cycles/min. 1 mL of the solution under release test was sampled and analyzed quantitatively by the HPLC method explained in the above Test Example 2, and the tube was supplemented with 1 mL of fresh phosphate buffer.

As a result, as shown in FIG. 4, initial release amount could be controlled by changing the ratio of drug to polymer and the release rate could be maintained constantly. However, the commercially available product, Risperdal Consta, did not release the drug actually for 14 days and started to release thereafter.

In addition, as shown in FIG. 5, it can be known that the release rate of the drug decreased when the molecular weight of the polymer increased while fixing the ratio of drug to the polymer constantly. This means that the release rate of the drug can be controlled by adjusting the molecular weight of the polymer. Meanwhile, from Comparative Examples, it can be confirmed that the release was delayed by several days to several weeks although the period varied depending on molecular weight.

The invention claimed is:

1. A sustained-release microparticle containing a poorly water-soluble drug, consisting essentially of the poorly water-soluble drug and a multivalent metal ion salt of polylactic acid having at least one terminal carboxyl group or a derivative thereof, wherein the poorly water-soluble drug is entrapped in the multivalent metal ion salt of polylactic acid or a derivative thereof, and the polylactic acid having at least one terminal carboxyl group or a derivative thereof has an average molecular weight number from 500 to 5,000 daltons.

2. The sustained-release microparticle containing a poorly water-soluble drug according to claim 1, wherein the polylactic acid having at least one terminal carboxyl group or a derivative thereof is selected from the group consisting of compounds represented by Formulae 1 to 6 below:

  [Formula 1]

wherein A is —COO—CHZ—; B is —COO—CHY—, —COO—CH$_2$CH$_2$CH$_2$CH$_2$CH$_2$— or —COO—CH$_2$CH$_2$OCH$_2$—; R is hydrogen atom, or acetyl group, benzoyl group, decanoyl group, palmitoyl group, methyl group, or ethyl group; each of Z and Y independently is hydrogen atom, methyl group or phenyl group; M is independently H, Na, K, or Li; n is an integer of 1 to 30; and m is an integer of 0 to 20;

  [Formula 2]

wherein X is methyl group; Y' is hydrogen atom or phenyl group; p is an integer of 0 to 25 and q is an integer of 0 to 25 provided that p+q is an integer of 5 to 25; R is hydrogen atom, acetyl group, benzoyl group, decanoyl group, palmitoyl group, methyl group or ethyl group; Z is hydrogen atom, methyl group or phenyl group; and M is independently H, Na, K, or Li;

  [Formula 3]

wherein W-M' is

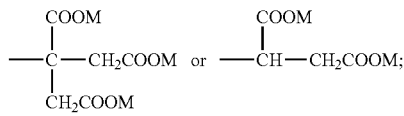

PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one; R is hydrogen atom, acetyl group, benzoyl group, decanoyl group, palmitoyl group, methyl group or ethyl group; and M is independently H, Na, K, or Li;

  [Formula 4]

wherein S is

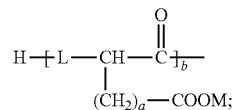

L is —NR$_1$— or -0- in which R$_1$ is hydrogen atom or C$_{1\text{-}10}$ alkyl; Q is CH$_3$, CH$_2$CH$_3$, CH$_2$CH$_2$CH$_3$, CH$_2$CH$_2$CH$_2$CH$_3$, or CH$_2$C$_6$H$_5$; a is an integer of 0 to 4; b is an integer of 1 to 10; M is H, Na, K, or Li; PAD is one or more selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one;

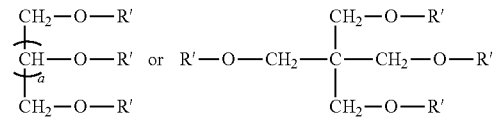

[Formula 5]

wherein R' is —PAD-O—C(O)—CH$_2$CH$_2$—C(O)—OM, in which PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one, and M is H, Na, K, or Li; and a is an integer of 1 to 4;

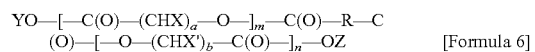  [Formula 6]

wherein each of X and X' is independently hydrogen, alkyl or aryl; each of Y and Z is independently H, Na, K, or Li; each of m and n is independently an integer of 0 to 95, provided that 5<m+n<100; each of a and b is independently an integer of 1 to 6; R is substituted or unsubstituted —(CH$_2$)$_k$— in which k is an integer of 0 to 10, divalent alkenyl having 2 to 10 carbon atoms, divalent aryl having 6 to 20 carbon atoms, or a combination thereof.

3. The sustained-release microparticle containing a poorly water-soluble drug according to claim 1, wherein the multivalent metal ion is one or more selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$ and $Al^{3+}$.

4. The sustained-release microparticle containing a poorly water-soluble drug according to claim 1, which has a particle diameter of 1 to 400 μm.

5. The sustained-release microparticle containing a poorly water-soluble drug according to claim 1, wherein the content of the poorly water-soluble drug is 1 to 50% by weight with respect to the total weight of the microparticle.

6. The sustained-release microparticle containing a poorly water-soluble drug according to claim 1, wherein the poorly water-soluble drug is one or more selected from the group consisting of olanzapine, risperidone, ziprasidone, rivastigmine, naloxone, naltrexone, sirolimus, tacrolimus, carmustine, progesterone, estrogen, estradiol, levonorgestrel and norethisteron.

7. A method for preparing a sustained-release microparticle containing a poorly water-soluble drug, comprising:
   i) preparing a polymer-drug solution containing a monovalent metal salt of polylactic acid having at least one terminal carboxyl group or a derivative thereof and the poorly water-soluble drug in an organic solvent; and
   ii) dispersing the polymer-drug solution in an aqueous solution containing a multivalent metal ion and optionally a surfactant to form a microparticle,
   wherein the polylactic acid having at least one terminal carboxyl group or a derivative thereof has an average molecular weight number from 500 to 5,000 daltons.

8. The method for preparing a sustained-release microparticle containing a poorly water-soluble drug according to claim 7, wherein the monovalent metal salt of polylactic acid or a derivative thereof is selected from the group consisting of compounds of Formulae 1 to 6 defined in claim 1, in which M is Na, K or Li.

9. The method for preparing a sustained-release microparticle containing a poorly water-soluble drug according to claim 7, wherein the organic solvent is selected from the group consisting of dichloromethane, hexafluoroisopropanol, ethyl acetate, ethanol, methanol, dimethylformamide, acetone, acetonitrile, tetrahydrofuran, acetic acid, dimethyl sulfoxide, chloroform, methyl dichloroacetate, methyl chloroacetate, ethyl chloroacetate, ethyl dichloroacetate, methyl fluoroacetate, methyl difluoroacetate, ethyl fluoroacetate, ethyl difluoroacetate, ethyl acetate, methyl acetate, methyl formate, ethyl formate, isopropyl formate, propyl formate and mixtures thereof.

10. The method for preparing a sustained-release microparticle containing a poorly water-soluble drug according to claim 7, wherein the multivalent metal ion is one or more selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$ and $Al^{3+}$.

11. The method for preparing a sustained-release microparticle containing a poorly water-soluble drug according to claim 7, wherein the poorly water-soluble drug is one or more selected from the group consisting of olanzapine, risperidone, ziprasidone, rivastigmine, naloxone, naltrexone, sirolimus, tacrolimus, carmustine, progesterone, estrogen, estradiol, levonorgestrel and norethisteron.

12. The method for preparing a sustained-release microparticle containing a poorly water-soluble drug according to claim 7, further comprising:
   iii) obtaining the microparticle formed in step ii) and washing it with water.

13. The method for preparing a sustained-release microparticle containing a poorly water-soluble drug according to claim 12, further comprising:
   iv) freeze-drying the microparticle washed in step iii).

14. A sustained-release microparticle containing a poorly water-soluble drug, consisting essentially of the poorly water-soluble drug and a multivalent metal ion salt of polylactic acid having at least one terminal carboxyl group or a derivative thereof, wherein the poorly water-soluble drug is entrapped in the multivalent metal ion salt of polylactic acid or a derivative thereof, the polylactic acid having at least one terminal carboxyl group or a derivative thereof has an average molecular weight number from 500 to 5,000 daltons, wherein the multivalent metal ion is one or more selected from the group consisting of $Ca^{2+}$, $Mg^{2+}$, $Ba^{2+}$, $Cr^{3+}$, $Fe^{3+}$, $Mn^{2+}$, $Ni^{2+}$, $Cu^{2+}$, $Zn^{2+}$ and $Al^{3+}$, wherein the polylactic acid having at least one terminal carboxyl group or a derivative thereof is selected from the group consisting of compounds represented by Formulae 1 to 6 below:

  [Formula 1]

wherein A is —COO—CHZ—; B is —COO—CHY—, —COO—CH$_2$CH$_2$CH$_2$CH$_2$CH$_2$— or —COO—CH$_2$CH$_2$OCH$_2$; R is hydrogen atom, or acetyl group, benzoyl group, decanoyl group, palmitoyl group, methyl group, or ethyl group; each of Z and Y independently is hydrogen atom, methyl group or phenyl group; M is independently H, Na, K, or Li; n is an integer of 1 to 30; and m is an integer of 0 to 20;

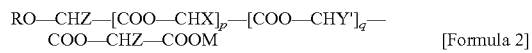  [Formula 2]

wherein X is methyl group; Y' is hydrogen atom or phenyl group; p is an integer of 0 to 25 and q is an integer of 0 to 25 provided that p+q is an integer of 5 to 25; R is hydrogen atom, acetyl group, benzoyl group, decanoyl group, palmitoyl group, methyl group or ethyl group; Z is hydrogen atom, methyl group or phenyl group; and M is independently H, Na, K, or Li;

  [Formula 3]

wherein W-M' is

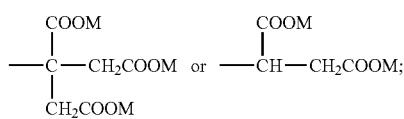

PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one; R is hydrogen atom, acetyl group, benzoyl group, decanoyl group, palmitoyl group, methyl group or ethyl group; and M is independently H, Na, K, or Li;

  [Formula 4]

wherein S is

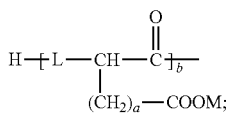

L is —$NR_1$— or -O- in which $R_1$ is hydrogen atom or $C_{1-10}$ alkyl; Q is $CH_3$, $CH_2CH_3$, $CH_2CH_2CH_3$, $CH_2CH_2CH_2CH_3$, or $CH_2C_6H_5$; a is an integer of 0 to 4; b is an integer of 1 to 10; M is H, Na, K, or Li; PAD is one or more selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one;

[Formula 5]

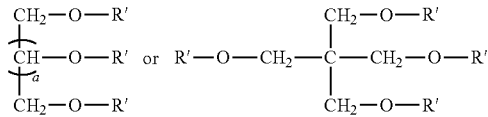

wherein R' is -PAD-O—C(O)—$CH_2CH_2$—C(O)—OM, in which PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one, and M is H, Na, K, or Li; and a is an integer of 1 to 4;

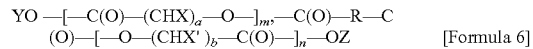

wherein each of X and X' is independently hydrogen, alkyl or aryl; each of Y and Z is independently H, Na, K, or Li; each of m and n is independently an integer of 0 to 95, provided that 5<m+n<100; each of a and b is independently an integer of 1 to 6; R is substituted or unsubstituted —$(CH_2)_k$—in which k is an integer of 0 to 10, divalent alkenyl having 2 to 10 carbon atoms, divalent aryl having 6 to 20 carbon atoms, or a combination thereof, wherein the multivalent metal ion salt of polylactic acid or a derivative thereof is contained in an amount of 50 to 99% by weight of a total weight of the microparticle, and wherein the microparticle has an amorphous or spherical shape.

15. The sustained-release microparticle containing a poorly water-soluble drug according to claim 14, which has a particle diameter of 1 to 400 μm.

16. The sustained-release microparticle containing a poorly water-soluble drug according to claim 14, wherein the content of the poorly water-soluble drug is 1 to 50% by weight with respect to the total weight of the microparticle.

17. The sustained-release microparticle containing a poorly water-soluble drug according to claim 14, wherein the poorly water-soluble drug is one or more selected from the group consisting of olanzapine, risperidone, ziprasidone, rivastigmine, naloxone, naltrexone, sirolimus, tacrolimus, carmustine, progesterone, estrogen, estradiol, levonorgestrel and norethisteron.

\* \* \* \* \*